United States Patent
Cooke et al.

(10) Patent No.: US 6,294,788 B1
(45) Date of Patent: Sep. 25, 2001

(54) RANDOMS CORRECTION IN POSITRON IMAGING

(75) Inventors: Steven E. Cooke, Garfield Heights; Christopher G. Matthews, Lyndhurst; John F. Vesel, Christina Dr., all of OH (US)

(73) Assignee: Marconi Medical Systems, Inc., Highland Heights, OH (US)

( * ) Notice: Subject to any disclaimer, the term of this patent is extended or adjusted under 35 U.S.C. 154(b) by 0 days.

(21) Appl. No.: 09/377,009

(22) Filed: Aug. 18, 1999

(51) Int. Cl.[7] .................................................. G01T 1/172
(52) U.S. Cl. .............................. 250/363.03; 250/363.07; 250/369
(58) Field of Search .................. 250/363.03, 363.07, 250/369; 378/7

(56) References Cited

U.S. PATENT DOCUMENTS

| | | | |
|---|---|---|---|
| 4,181,855 | * | 1/1980 | Horrocks .......................... 250/363.01 |
| 5,608,221 | * | 3/1997 | Bertelsen et al. ............... 250/363.03 |
| 5,793,045 | | 8/1998 | DiFilippo, et al. .............. 250/363.03 |
| 5,834,779 | | 11/1998 | Shao, et al ....................... 250/363.03 |
| 5,900,636 | * | 5/1999 | Nellemann et al. ............ 250/363.04 |
| 5,969,358 | * | 10/1999 | DiFulippo et al. ............. 250/363.03 |
| 5,998,793 | * | 12/1999 | Shao et al. ............................ 250/369 |
| 6,008,493 | * | 12/1999 | Shao et al. ....................... 250/363.04 |
| 6,057,551 | * | 5/2000 | Tararine .......................... 250/363.03 |
| 6,140,650 | * | 10/2000 | Berlad .............................. 250/363.09 |
| 6,198,104 | * | 3/2001 | Geagan et al. .................. 250/363.04 |

FOREIGN PATENT DOCUMENTS

| | | | | |
|---|---|---|---|---|
| 2-227691 | * | 9/1990 | (JP) ............................... G01T/1/161 |
| 7-318654 | * | 12/1995 | (JP) ............................... G01T/1/161 |

OTHER PUBLICATIONS

*Principles of Nuclear Medicine*1995; Section 2 "Operational Guidelines" by Margaret E. Daube–Witherspoon; pp. 346–362.

"A Practical Method for Randoms Subtraction in Vol. Imaging PET from Detector Singles Countrate Measurements"; R. J. Smith and J. S. Karp; Department of Radiology, University of Pennsylvania; pp. 992–996.

* cited by examiner

*Primary Examiner*—Constantine Hannaher
*Assistant Examiner*—Albert Gagliardi
(74) *Attorney, Agent, or Firm*—John J. Fry

(57) ABSTRACT

In positron emission imaging, coincident gamma ray pairs are acquired and processed to generate an image. Random gamma ray pairs in the acquired coincidence data degrade the quality of the resultant image. The coincident gamma ray pairs are re-paired to generate non-coincident gamma ray pairs. The non-coincident pairs are used to correct for randoms in the acquired coincidence data. Alternately, singles gamma rays may be detected and paired with non-coincident single gamma rays to generate non-coincident pairs. These pairs may be used to correct for randoms in the acquired coincidence data.

28 Claims, 5 Drawing Sheets

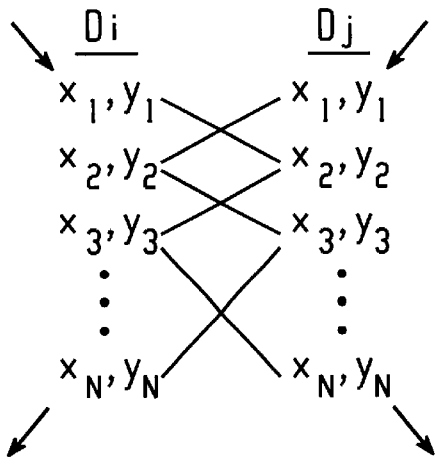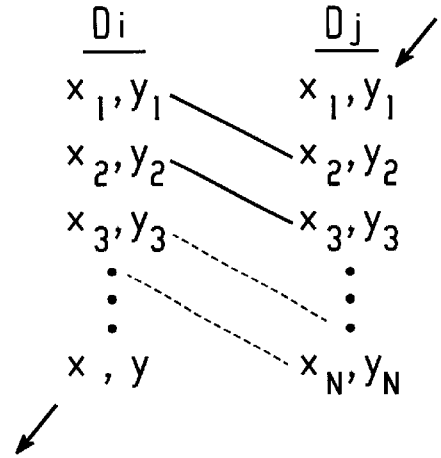
Fig. 4A       Fig. 4B
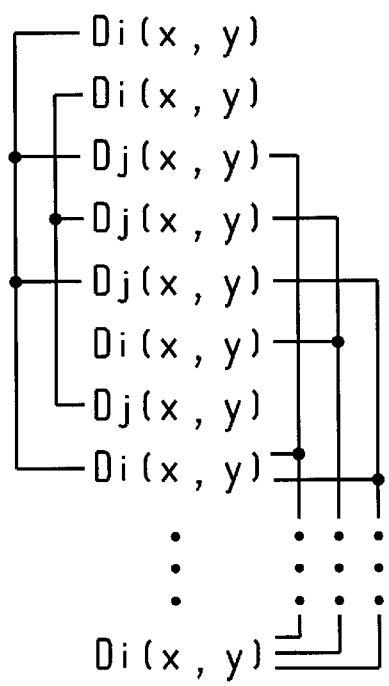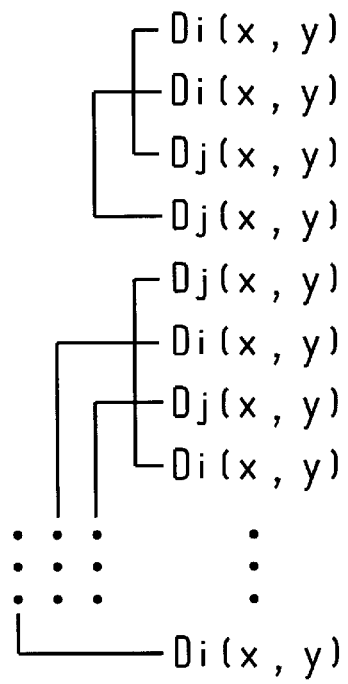
Fig. 4C       Fig. 4D

RANDOMS CORRECTION IN POSITRON IMAGING

BACKGROUND

The present invention relates to the field of positron imaging, and more particularly to the field of positron emission tomography. The invention is also applicable to other fields in where it is necessary to estimate the contribution of randoms in data indicative of positron coincidence events.

Positron emission tomography (PET) is a branch of nuclear medicine in which a positron-emitting radiopharmaceutical such as $^{18}$F-fluorodeoxyglucose (FDG) is introduced into the body of a patient. Each emitted positron reacts with an electron in what is known as an annihilation event, thereby simultaneously generating a pair of 511 keV gamma rays. The gamma rays are emitted in directions approximately 180° apart, i.e. in opposite directions.

A pair of detectors registers the position and energy of the respective gamma rays, thereby providing information as to the position of the annihilation event and hence the positron source. Because the gamma rays travel in opposite directions, the positron annihilation is said to have occurred along a line of response (LOR) connecting the detected gamma rays. A number of such events are collected and used to reconstruct a clinically useful image.

One factor which degrades image quality in PET imaging is random events. The 511 keV gamma rays generated by the positron annihilations are detected within a narrow coincidence timing window. Pairs of such gamma rays detected within this timing window are ordinarily considered to be coincident and are used to generate an image. However, some of these events result from what are known as random events. A random event is one in which a pair of gamma rays from two unrelated annihilation events are detected in coincidence. Thus, the acquired coincidence data includes both true and random events. Because the LORs for the random events do not represent actual positron annihilations, the randoms introduce noise into the acquired data, thereby degrading image quality.

Various techniques have been used to minimize the deleterious effects of random events. Because the number of randoms increases with the square of activity, one technique is to image at relatively low activity levels. While relatively fewer randoms are detected, an undesirable side effect of this technique is that fewer true coincidence events are available to generate the image.

Another technique for estimating the contribution of randoms is to delay the signal from one of the detectors by an amount longer than the coincidence timing window prior to applying the coincidence check. Due to the delay, events which are detected by a pair of detectors within the coincidence timing window (i.e., in coincidence) represent randoms. The collected events are rebinned and used to correct the acquired coincidence data. A particular drawback to such a delayed correction technique is that the rate of randoms collection is the same as that of the true event collection. This technique also has a deleterious effect on image noise characteristics.

Yet another technique is to determine the random coincidence rate based on the singles rates of the system's detectors and the length of the coincidence timing window. According to one technique, the system detectors have been treated as a plurality of virtual subdetectors, and the singles rate for each of the subdetectors has been measured. The singles rates for the various combinations of subdetectors has in turn been used to generate a randoms sinogram. One disadvantage to such a technique is that it is necessary to collect data additional to the desired coincidence data. Yet another disadvantage is that improving the accuracy of the estimation requires that the detectors be divided into arbitrarily small subdetectors.

SUMMARY

Aspects of the present invention address these matters, and others.

According to one aspect of the present invention, a method of position imaging includes receiving data indicative of a plurality of detected coincident gamma ray pairs, said pairs including positron annihilation gamma ray pairs and random gamma ray pairs, re-pairing gamma rays from the detected coincident gamma ray pairs so as to generate non-coincident gamma ray pairs, and using the coincident gamma ray pairs and the non-coincident gamma ray pairs to generate a randoms corrected image.

According to a more limited aspect, the step of receiving includes receiving a list of detected coincident gamma ray pairs and the step of re-pairing includes re-pairing gamma rays from the list of detected coincident gamma ray pairs.

According to another more limited aspect, step of re-pairing includes pairing each of a plurality of gamma rays with a non-coincident gamma ray. According to a still more limited aspect, the invention includes pairing each of a plurality of gamma rays with a plurality of non-coincident gamma rays. The non-coincident gamma rays may be paired in all possible combinations.

According to another more limited aspect of the present invention, the step of receiving includes receiving data indicative of coincident gamma ray pairs detected over a time period T. The method also includes rebinning the non-coincident gamma ray pairs and resealing the rebinned non-coincident gamma ray pairs to generate T*R pairs, where R is a randoms rate.

According to another limited aspect, the method includes combining the coincident and non-coincident gamma ray pairs and generating an image indicative of the combined coincident and non-coincident gamma ray pairs. The method may also include rebinning the coincident gamma ray pairs, rebinning the non-coincident gamma ray pairs, subtracting the rebinned non-coincident gamma ray pairs from the rebinned coincident gamma ray pairs to generate corrected coincidence data, and generating an image indicative of the corrected coincidence data.

According to still another limited aspect, the method includes using first and second detectors to detect coincident gamma ray pairs. The step of re-pairing includes pairing gamma rays detected by the first detector with non-coincident gamma rays detected by the second detector. According to a yet more limited aspect, the method method may include using first, second, and third detectors to detect coincident gamma rays and wherein the step of re-pairing includes pairing gamma rays detected by the first detector with gamma rays detected by the third detector and pairing gamma rays detected by the second detector with gamma rays detected by the third detector.

According to another aspect of the present invention, a method of randoms-corrected imaging includes detecting coincident gamma ray pairs, said pairs including positron annihilation gamma ray pairs and random gamma ray pairs, generating non-coincident gamma ray pairs, and using the coincident gamma ray pairs and the non-coincident gamma ray pairs to generate a randoms corrected image.

According to a more limited aspect, the step of generating non-coincident gamma ray pairs includes detecting a plurality of single gamma rays and pairing each of a plurality of the single gamma rays with a non-coincident single gamma ray. According to a still more limited aspect, the method may include detecting coincident gamma ray pairs for a time period T, establishing a randoms rate R, and detecting at least 2*T*R single gamma rays. According to a still more limited aspect, the method may include pairing each of a plurality of the gamma rays with a plurality of non-coincident gamma rays. According to a still more limited aspect, he method may include detecting coincident gamma ray pairs for time period T, determining a randoms rate R, and rescaling the non-coincident gamma ray pairs to generate T*R pairs. According to a still more limited aspect, the method may include rebinning the coincident gamma ray pairs, combining the rebinned non-coincident event pairs with the rebinned coincident gamma ray pairs to generate randoms corrected data, and generating an image from the randoms corrected data.

According to yet another limited aspect of the present invention, the step of detecting includes using first, second and third detectors to detect the coincident gamma ray pairs. The method also includes establishing a randoms rate for the first and third detectors, a randoms rate for the first and second detectors, and a randoms rate for the second and third detectors.

According to still another limited aspect, the step of generating includes re-pairing gamma rays from the coincident gamma ray pairs to generate non-coincident gamma ray pairs. According to a still more limited aspect, the method may include pairing each of a plurality of gamma rays with a non-coincident gamma ray. According to a still more limited aspect, the method may also include pairing each of a plurality of gamma rays with a plurality of non-coincident gamma rays, or in all possible non-coincident combinations.

According to another more limited aspect, the method includes rebinning the non-coincident gamma ray pairs and rescaling the rebinned non-coincident gamma ray pairs. According to a yet more limited aspect, the method includes rebinning the coincident gamma ray pairs, combining the rebinned coincident gamma ray pairs and the rebinned non-coincident event pairs to generate randoms corrected data, and generating an image from the randoms corrected data.

The method may also include generating a list of the coincident gamma ray pairs and including re-pairing gamma rays from the list of coincident gamma ray pairs to generate non-coincident event pairs.

According to another aspect of the present invention, an apparatus includes means for detecting coincident gamma ray pairs, said pairs including detected positron annihilation gamma ray pairs and detected gamma ray pairs; means for generating non-coincident gamma ray pairs, and means for generating a randoms corrected image based on the coincident gamma ray pairs and the non-coincident gamma ray pairs. According to a more limited aspect, the apparatus includes means for detecting a plurality of single gamma rays and means for pairing the single gamma rays to generate a plurality of non-coincident gamma ray pairs. According to a yet more limited aspect, the apparatus includes means for generating a list of the detected gamma ray pairs and means for re-pairing gamma ray pairs from the list of coincident gamma ray pairs so as to generate non-coincident gamma ray pairs. According to a still more limited aspect, the means for detecting comprises three radiation sensitive detectors disposed about an examination region.

FIGURES

FIGS. 4A, 4B, 4C, and 4D depict techniques for generating non-coincident gamma ray pairs.

Figure 5:
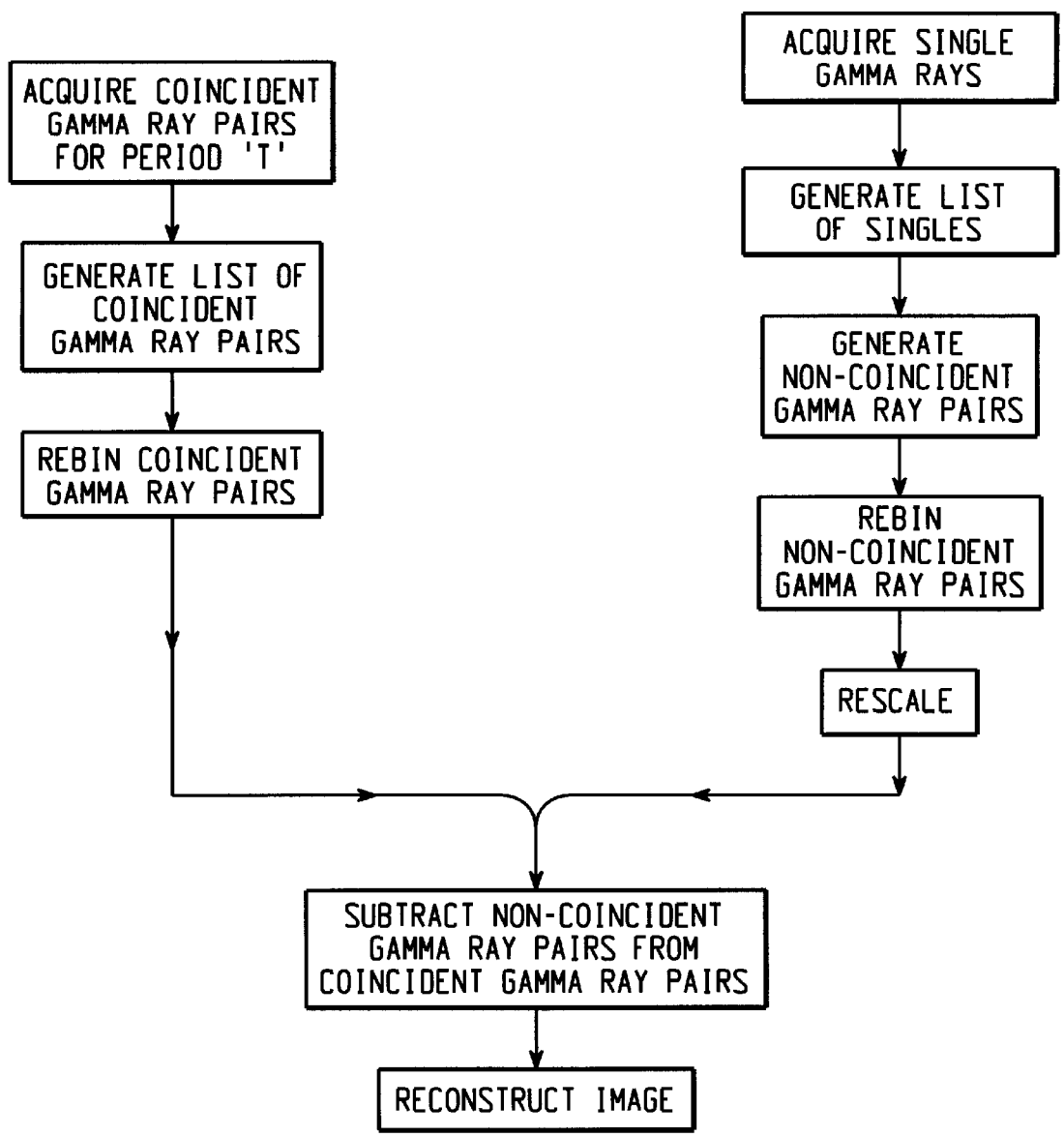

FIG. 5 depicts a technique for processing coincident and singles data.

Figure 6:
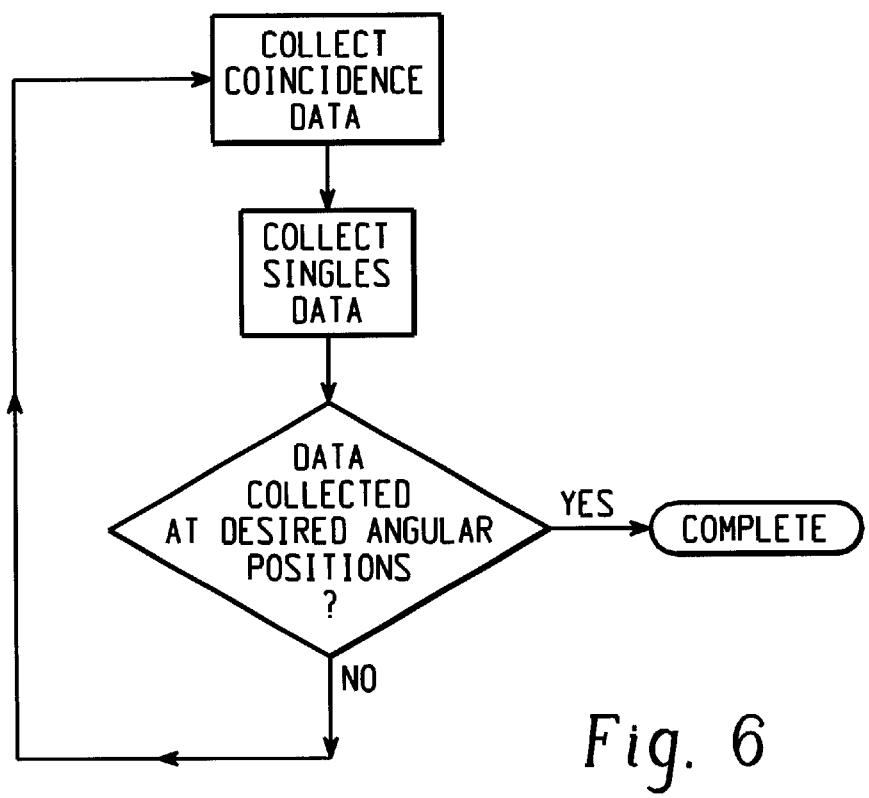

FIG. 6 depicts a technique for acquiring coincident and singles data.

DESCRIPTION

Figure 1:
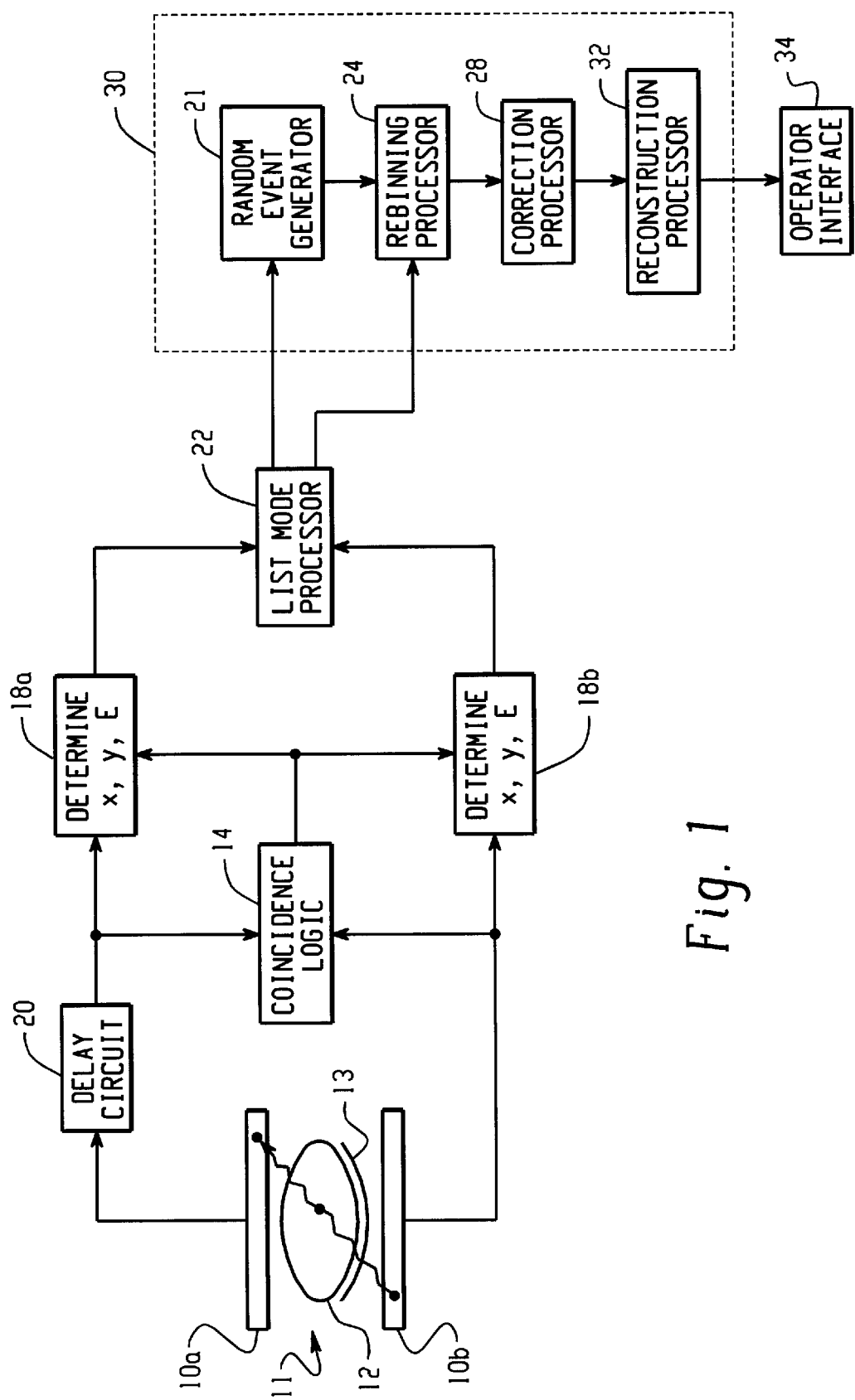
FIG. 1 is a block diagram of a gamma camera and imaging computer.

With reference to FIG. 1, a gamma camera includes a pair of radiation sensitive detectors 10a, 10b mounted to a gantry. The detectors 10a, 10b are located in opposed positions about an examination region 11. The examination region 11 is sized to accept an object being imaged, for example a human patient 12.

A patient support 13 supports the patient within the examination region. A drive selectively rotates the detectors 10a, 10b about the examination region 11 so as to permit acquisition of radiation data from a plurality of angular positions φ relative to the patient. The detectors 10a, 10b may be movable radially and/or tangentially with respect to the examination region 11, or movable to more than one angular position with respect to each other.

Each detector 10a, 10b includes a NaI(Tl) scintillator crystal, an x,y array of photomultiplier tubes (PMTs), and processing electronics. Axial septa disposed between the scintillator crystal and the examination region limit the axial acceptance angle of gamma radiation which reaches the scintillator. Energy from gamma rays striking the scintillator crystal is converted to light which is detected by one or more PMTs, thereby signaling a detected event.

Coincidence logic 14 determines whether events detected by both detectors 10a, 10b occurred simultaneously. More specifically, the coincidence logic determines whether both detectors detect a gamma ray within a coincidence time interval τ, for example on the order of 15 nS. In coincidence imaging, events which are detected outside the coincidence time interval are ordinarily rejected and not processed further.

A selectable delay circuit 20 delays the signals from one of the detectors by an amount longer than that of the coincidence time interval, for example, on the order of 1 μS. The delay circuit 20 is ordinarily disabled during the acquisition of coincidence data but may be selectively enabled as described more fully below.

Associated with each detector 10 is energy and position determining circuitry 18a, 18b which determines the position x,y and energy E of the detected events. A list mode processor 22 generates a list of the detected events. Some of the events may be rejected prior to or after list mode processing based on the energy E of the gamma rays or other criteria as is known in the art.

In coincidence imaging, the list contains a plurality of coincident gamma ray pairs and can be represented as follows:

$$D_i(x_1, y_1); D_j(x_1, y_1)$$
$$D_i(x_2, y_2); D_j(x_2, y_2)$$
$$D_i(x_3, y_3); D_j(x_3, y_3)$$
$$D_i(x_N, y_N); D_j(x_N, y_N)$$

where $D_x$ identifies the detector 10a, 10b, and x, y are the coordinates of the gamma ray. Of course, additional or different data (e.g., the energy of the detected gamma rays, the angular position of the detectors) may be included in the list or in associated headers and used in further processing. The output of the list mode processor 22 is preferably stored in a memory for further processing at a convenient time, for example, after data acquisition for a particular patient has been completed.

Figure 2:
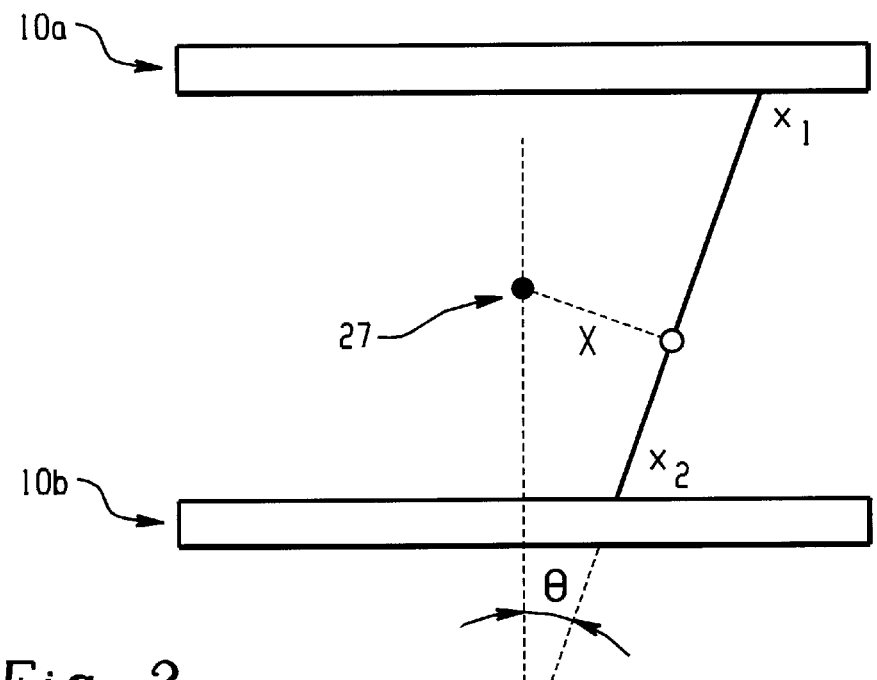
FIGS. 2 illustrates transverse rebinning.

Further processing is preferably accomplished using a conventional imaging computer 30. A rebinning processor 24 sorts coincident gamma ray pairs based on the x, y locations of the detected gamma rays and angular position $\phi$ of the detectors 10 to generate sinograms. With reference to FIG. 2, a point such as the center 27 of the imaging region is defined. The transverse coordinates $x_1$, $x_2$ are used to calculate a transverse coordinate X relation to the center 27 and transverse angle $\theta$ in relation to a defined stationary coordinate system. While other rebinning techniques may be employed, the foregoing facilitates the generation of conventional sinograms. The gamma ray pairs are preferably rebinned in the axial direction using a single slice rebinning technique, although other axial rebinning techniques may be employed.

Returning to FIG. 1, a random event generator 21 generates non-coincident gamma ray pairs based on the acquired radiation data. The non-coincident pairs are rebinned by the rebinning processor 24 in a manner analogous to that described above for the coincident gamma ray pairs. A randoms correction processor 28 accepts the rebinned coincident ray pairs and non-coincident gamma ray pairs and generates randoms corrected data. A reconstruction processor 32 processes the corrected data using techniques such as filtered back projection or iterative reconstruction to generate images indicative of the detected events. For example, a plurality of axial tomographic image slices may be generated. Other techniques such as focal plane imaging may also be employed. An operator interface 34 such as a monitor or printer is used to display the images in human readable form.

A suitable gamma camera having two detectors 10 is an Axis™ with γPET™ option gamma camera available from Picker International, Inc. of Highland Heights, Ohio. A suitable imaging computer is the Odyssey™ FX computer also available from Picker International.

Figure 3:
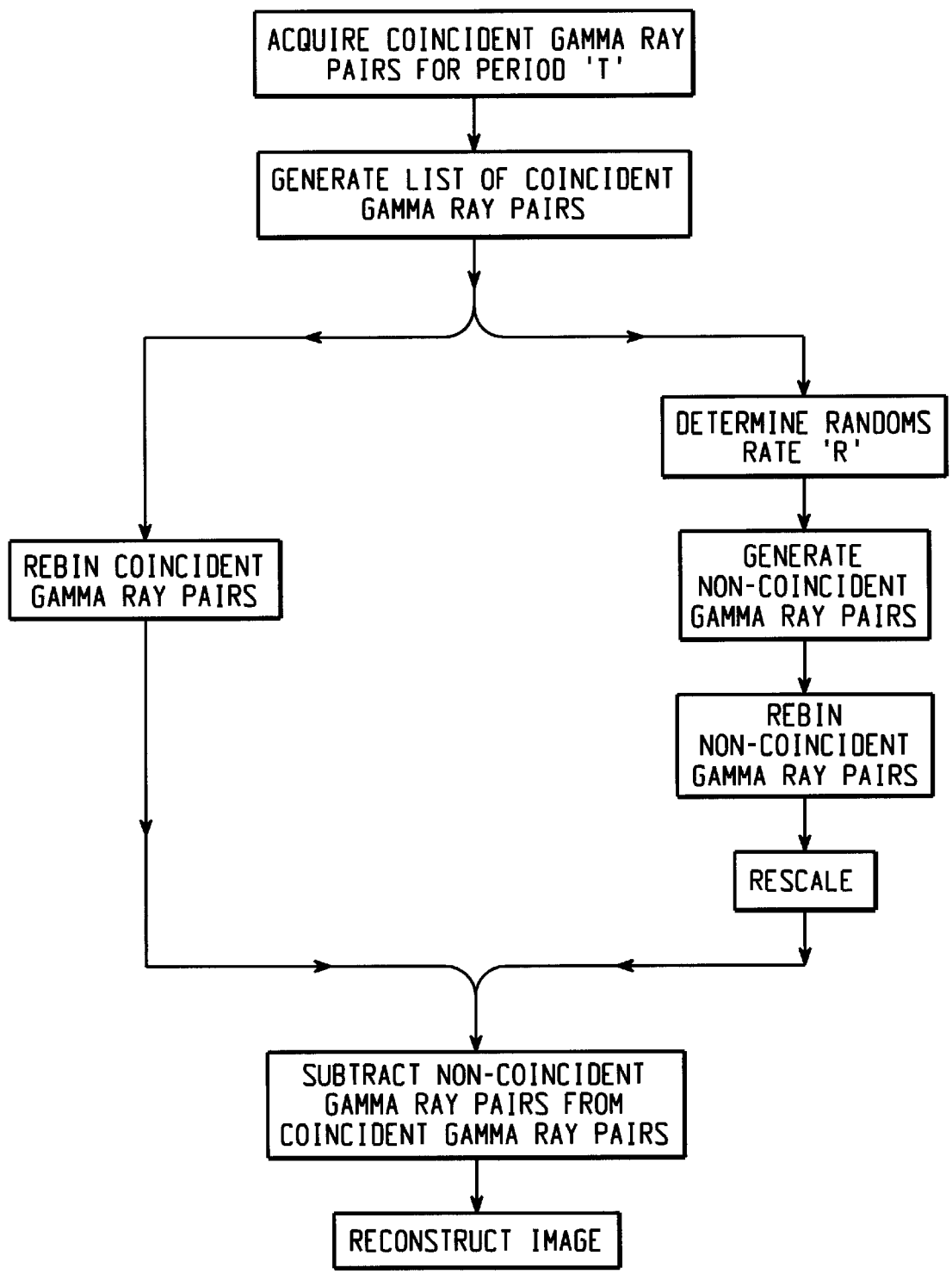
FIG. 3 depicts a technique for processing coincident gamma ray data.

In operation, and with reference to FIG. 3, coincident gamma ray pairs are acquired for time period T with the delay circuit 20 disabled to acquire a total of N coincident pairs. The acquired data includes gamma ray pairs indicative of positron annihilation events as well as random gamma ray pairs. List mode data indicative of the acquired coincident gamma ray pairs is generated, and the randoms rate R is determined. This process is repeated with the detectors 10 located at a plurality of angular positions $\phi$. The generated list mode data is preferably stored until scanning of the patient is completed.

The list mode data is rebinned for further processing. Non-coincident gamma ray pairs are generated, rebinned, and rescaled (if necessary) so that T*R non-coincident pairs are created. The rebinned non-coincident gamma ray pairs are subtracted from the rebinned gamma ray pairs to correct for randoms in the acquired coincident data. The resultant corrected data is used to reconstruct an image.

The randoms rate R is determined by enabling the delay line 20 and counting the coincidences for a relatively short period of time (e.g., 1 second) to establish a coincidence rate. It should be noted that it is unnecessary to process the detected gamma rays except to the extent necessary for determining the randoms rate. Alternately, the randoms rate R may be determined based on the measured the singles rate for each detector 10:

$$R = 2\tau S_1 S_2$$

where
  $S_1$ = measured singles rate for detector 1; and
  $S_2$ = measured singles rate for detector 2.

Where the randoms rate R is determined by measurement of the detector singles rates, the delay circuit 20 is unnecessary and need not be included in the system when operating in list mode. The randoms rate R and/or the singles rate $S_x$ may be determined by the gamma camera and passed on to the imaging computer in a header or otherwise as part of the list mode data.

Various techniques may be used to generate the non-coincident gamma ray pairs. With reference to FIGS. 4A and FIG. 4B, randoms data may be generated based on the coincident gamma ray pairs acquired during data acquisition. In particular, the gamma rays in the list of coincident gamma ray pairs may be paired with gamma rays from other gamma ray pairs in the list.

Turning to FIG. 4A, each of a plurality of gamma rays detected by detector $D_i$ is paired with a plurality of gamma rays detected by detector $D_j$. All possible pairings, with the exception of gamma rays within each coincident pair (which are likely to represent trues), are generated. This technique yields approximately $$N^2 - N$$

random events. Alternately, each of the plurality of gamma rays detected by detector $D_i$ may be paired with a plurality, but less than all, of the gamma rays detected by detector $D_j$.

Another technique for generating randoms data based on the acquired coincidence data is shown in FIG. 4B. Each of a plurality of gamma rays detected by detector $D_i$ is paired with a gamma ray detected by detector $D_j$. While FIG. 4B shows each gamma ray paired with one gamma ray from the next coincident pair in the list (i.e. an offset of 1), other offsets may be used to increase the temporal offset between the individual events which make up the pair. For example, an offset of approximately 10 yields a temporal offset on the order of several microseconds, depending on the coincidence count rate of the gamma camera and the activity of the source. This technique yields N random combinations.

Those skilled in the art will recognize that other pairing techniques may readily be implemented. By way of example, the events may be paired based on a random or other algorithm.

Each of the non-coincident gamma ray pairs is characterized by a LOR analogous to that of the coincident gamma ray pairs. The non-coincident pairs are rebinned as described above for the acquired coincidence events. The generated randoms are rescaled so that the total number of randoms is equal to T*R, and the rescaled random data is used to correct the acquired coincident mode data. Using the example described in FIG. 4A, an appropriate rescaling factor is $$\frac{T*R}{N^2 - N}$$

For the example of FIG. 4B, an appropriate rescaling factor is $$\frac{T*R}{N}$$

Randoms data may also be generated based on acquired single gamma rays. Turning to FIG. 5, coincident gamma ray pairs are acquired for period N and a list of the coincident pairs is generated. Single gamma rays are likewise acquired and a list of the singles is generated.

With reference to FIG. 6, acquisition of singles data is may be interleaved with acquisition of the coincidence data. After coincidence data is acquired at a particular angular position φ, the coincidence logic circuitry is disabled and singles data is collected until 2*T*R events (or another desired number) have been acquired. If the gamma camera system is capable of detecting singles data during the coincidence acquisition, the coincidence circuitry need not be disabled and the singles data may be collected concurrently with the collection of the coincidence data. Poisson noise can be reduced by acquiring a larger number of singles. Because the singles data is acquired relatively quickly, a suitable data set may also be collected by acquiring singles over a relatively short fixed time period, for example on the order of one second. The detectors are rotated to the next angular position, and the process repeated until data has been acquired at each of the desired angular positions.

Returning to FIG. 5, non-coincident gamma ray pairs are generated by pairing non-coincident events, rebinning and (if necessary) rescaling. The non-coincident pairs are subtracted from the coincident pairs and used to reconstruct an image.

The list mode singles data may be visualized as follows:

$D_i(x, y), \phi$ $D_j(x, y), \phi$ $D_j(x, y), \phi$ $D_i(x, y), \phi$ $D_i(x, y), \phi$ $D_j(x, y), \phi$ $\vdots$ $D_j(x, y), \phi$ $D_i(x, y), \phi$ It will be appreciated that events detected by detectors $D_i$, $D_j$, which are not adjacent in the list will not represent coincident gamma ray pairs.

Turning now to FIG. 4C, the acquired singles data may be used to generate randoms data in a manner analogous to that described in connection with FIG. 4A above. Each of a plurality of singles detected by detector $D_i$ is paired with a plurality of singles detected by detector $D_j$. All possible pairings, with the exception of those based on singles which were detected in temporal proximity (and are therefore likely to represent true coincidence events) are generated. Assuming that each detector receives an equal number of events, this technique yields somewhat less than $$\left(\frac{N}{2}\right)^2 - \frac{N}{2}$$

random events, where N is the number of detected singles. Alternately, each of a plurality of the gamma rays detected by $D_i$ may be paired with a plurality, but less than all, of the non-coincident gamma rays detected by detector $D_j$.

Turning now to FIG. 4D, the acquired singles data may be used to generate randoms data in a manner analogous to that described in connection with FIG. 4B above. Each of a plurality of single gamma rays detected by detector $D_i$ is paired with a single detected by detector $D_j$. While FIG. 4, again with a temporal offset to avoid generating trues. While the offset is shown as being one for ease of illustration, other offsets can be used. This technique yields N/2 random combinations.

Those skilled in the art will recognize that other pairing techniques may readily be implemented. By way of example, the events may be paired based on a random or other algorithm.

The generated randoms data contains a plurality of paired events. Each paired event is characterized by a LOR analogous to that of the acquired coincidence events. Accordingly, these events are rebinned in a manner analogous to that described above for the acquired coincidence events. While other rebinning techniques may be employed, the foregoing facilitates the generation of conventional sinograms.

The non-coincident pairs are used to correct the coincident pairs. In particular, the rebinned non-coincident pairs are subtracted from the rebinned coincidence pair sinogram prior to image reconstruction. Alternately, separate coincidence and generated randoms images may be generated, and the randoms images subtracted from the coincidence image to generate a randoms free image.

While the foregoing discussion has focused on a gamma camera system having two detectors 10, data from gamma cameras having three or more detectors may also be used. Similarly, the technique is applicable to gamma cameras whose detectors are disposed in a variety of configurations, such as opposed, orthogonal, equal angular intervals, and the like. The technique may also be applied to conventional ring type PET scanners wherein a plurality of detectors are disposed in a ring about the examination region.

In a gamma camera having three detectors, the randoms rate R may be estimated for each pair of detectors (e.g., $D_1D_2$, $D_2D_3$, $D_1D_3$) by selectively applying a delay line to two of the three detectors in sequence and counting the coincidence rate with respect to the undelayed detectors. Alternately, the randoms rate $R_{ij}$ may be estimated by counting the singles rate for each combination of detectors:

$R_{12} = 2\tau S_1 S_2$ $R_{23} = 2\tau S_2 S_3$ $R_{13} = 2\tau S_1 S_3$ where $S_1$=measured singles rate for detector 1

$S_2$=measured singles rate for detector 2

$S_3$—measured singles rate for detector 3.

Random events are likewise generated in a manner analogous to that described above for a two detector system, except that randoms data is generated for each combination of detectors (e.g., $D_1D_2$, $_{D1}D_3$, $_{D2}D_3$).

The technique is also not limited to systems operating in the list mode and may be implemented where data is rebinned using the so-called "on the fly" method. The coincidence data is acquired and rebinned in the normal fashion. However, the non-coincident pairs may be generated by temporarily storing events from one of the detectors 10 and pairing each stored event with a subsequent event from another of the detectors 10. Thus, the $m^{th}$ event detected by detector $D_i$ may be paired with the $(m+n)^{th}$ event detected by detector $D_j$, where n is a desired temporal offset. The generated events are rebinned as described above on an on the fly basis in a separate sinogram which is rescaled (if necessary) and subtracted from the coincidence data subtracted from (rather than added to) the coincidence data to generated a corrected data set.

The invention has been described with reference to the preferred embodiments. Obviously, modifications and alterations will occur to others upon reading and understanding the preceding description. It is intended that the invention be construed as including all such modifications an alterations insofar as they come within the scope of the appended claims or the equivalents thereof.

What is claimed is:

1. A method of position imaging comprising:
   receiving data indicative of a plurality of detected coincident gamma ray pairs, said pairs including positron annihilation gamma ray pairs and random gamma ray pairs;
   re-pairing gamma rays from the detected coincident gamma ray pairs so as to generate non-coincident gamma ray pairs;
   using the coincident gamma ray pairs and the non-coincident gamma ray pairs to generate a randoms corrected image.

2. The method of claim 1 wherein the step of receiving includes receiving a list of detected coincident gamma ray pairs and wherein the step of re-pairing includes re-pairing gamma rays from the list of detected coincident gamma ray pairs.

3. The method of claim 1 wherein the step of re-pairing includes pairing each of a plurality of gamma rays with a non-coincident gamma ray.

4. The method of claim 3 including pairing each of a plurality of gamma rays with a plurality of non-coincident gamma rays.

5. The method of claim 4 including pairing non-coincident gamma rays in all possible combinations.

6. The method of claim 3 wherein the step of receiving includes receiving a data indicative of coincident gamma ray pairs detected over a time period T and further including
   rebinning the non-coincident gamma ray pairs;
   rescaling the rebinned non-coincident gamma ray pairs to generate T*R pairs, where R is a randoms rate.

7. The method of claim 1 including
   combining the coincident and non-coincident gamma ray pairs;
   generating an image indicative of the combined coincident and non-coincident gamma ray pairs.

8. The method of claim 7 including
   rebinning the coincident gamma ray pairs;
   rebinning the non-coincident gamma ray pairs;
   subtracting the rebinned non-coincident gamma ray pairs from the rebinned coincident gamma ray pairs to generate corrected coincidence data;
   generating an image indicative of the corrected coincidence data.

9. The method of claim 1 including using first and second detectors to detect coincident gamma ray pairs and wherein the step of re-pairing includes pairing gamma rays detected by the first detector with non-coincident gamma rays detected by the second detector.

10. The method of claim 9 including using first, second, and third detectors to detect coincident gamma rays and wherein the step of re-pairing includes pairing gamma rays detected by the first detector with gamma rays detected by the third detector and pairing gamma rays detected by the second detector with gamma rays detected by the third detector.

11. A method of randoms-corrected imaging comprising:
    detecting coincident gamma ray pairs, said pairs including positron annihilation gamma ray pairs and random gamma ray pairs;
    generating non-coincident gamma ray pairs;
    using the coincident gamma ray pairs and the non-coincident gamma ray pairs to generate a randoms corrected image.

12. The method of claim 11 wherein the step of generating non-coincident gamma ray pairs includes
    detecting a plurality of single gamma rays; and
    pairing each of a plurality of the single gamma rays with a non-coincident single gamma ray.

13. The method of claim 12 including
    detecting coincident gamma ray pairs for a time period T;
    establishing a randoms rate R;
    detecting at least 2*T*R single gamma rays.

14. The method of claim 13 including pairing each of a plurality of the gamma rays with a plurality of non-coincident gamma rays.

15. The method of claim 14 including
    detecting coincident gamma ray pairs for time period T;
    determining a randoms rate R;
    resealing the non-coincident gamma ray pairs to generate T*R pairs.

16. The method of claim 15 including
    rebinning the coincident gamma ray pairs;
    combining the rebinned non-coincident event pairs with the rebinned coincident gamma ray pairs to generate randoms corrected data;
    generating an image from the randoms corrected data.

17. The method of claim 13 wherein the step of detecting includes using first, second and third detectors to detect the coincident gamma ray pairs and including establishing a randoms rate for the first and third detectors, a randoms rate for the first and second detectors, and a randoms rate for the second and third detectors.

18. The method of claim 11 wherein the step of generating includes re-pairing gamma rays from the coincident gamma ray pairs to generate non-coincident gamma ray pairs.

19. The method of claim 18 including pairing each of a plurality of gamma rays with a non-coincident gamma ray.

20. The method of claim 19 including pairing each of a plurality of gamma rays with a plurality of non-coincident gamma rays.

21. The method of claim 20 including pairing the gamma rays in all possible non-coincident combinations.

22. The method of claim 18 including
    rebinning the non-coincident gamma ray pairs;
    rescaling the rebinned non-coincident gamma ray pairs.

23. The method of claim 22 including
    rebinning the coincident gamma ray pairs;

combining the rebinned coincident gamma ray pairs and the rebinned non-coincident event pairs to generate randoms corrected data;

generating an image from the randoms corrected data.

24. The method of claim 18 including generating a list of the coincident gamma ray pairs and including re-pairing gamma rays from the list of coincident gamma ray pairs to generate non-coincident event pairs.

25. An apparatus comprising:

means for detecting coincident gamma ray pairs, said pairs including detected positron annihilation gamma ray pairs and detected gamma ray pairs;

means for generating non-coincident gamma ray pairs;

means for generating a randoms corrected image based on the coincident gamma ray pairs and the non-coincident gamma ray pairs.

26. The apparatus of claim 25 including means for detecting a plurality of single gamma rays;

means for pairing the single gamma rays to generate a plurality of non-coincident gamma ray pairs.

27. The apparatus of claim 25 including means for generating a list of the detected gamma ray pairs;

means for re-pairing gamma ray pairs from the list of coincident gamma ray pairs so as to generate non-coincident gamma ray pairs.

28. The apparatus of claim 25 wherein the means for detecting comprises three radiation sensitive detectors disposed about an examination region.

* * * * *